United States Patent [19]
Löfsjögård Nilsson et al.

[11] Patent Number: 5,209,654
[45] Date of Patent: May 11, 1993

[54] FLUID PUMP WITH FLEXIBLE PUMP CHAMBER

[76] Inventors: Erling Löfsjögård Nilsson, Vitmårvägen 77, S-194 60 Upplands Väsby; Jorge Inacio, Björnstigen 105, S-171 72 Solna, both of Sweden

[21] Appl. No.: 834,291
[22] PCT Filed: Sep. 14, 1990
[86] PCT No.: PCT/SE90/00585
§ 371 Date: Feb. 24, 1992
§ 102(e) Date: Feb. 24, 1992
[87] PCT Pub. No.: WO91/04063
PCT Pub. Date: Apr. 4, 1991

[30] Foreign Application Priority Data
Sep. 15, 1989 [SE] Sweden .................... 8903039
Sep. 15, 1989 [SE] Sweden .................... 8903040

[51] Int. Cl.[5] ................................................ F04B 43/08
[52] U.S. Cl. ....................................... 717/478; 417/394
[58] Field of Search ............... 417/478, 394, 472, 473; 600/16, 18

[56] References Cited
U.S. PATENT DOCUMENTS

| | | | |
|---|---|---|---|
| 3,568,659 | 3/1971 | Karnegis | 600/18 |
| 3,827,828 | 8/1974 | Edwards | 417/43 |
| 4,058,855 | 11/1977 | Runge | 3/1.7 |
| 4,781,716 | 11/1988 | Richelsoph | 600/16 |
| 4,840,205 | 6/1989 | Drevfors et al. | 417/472 |
| 4,925,377 | 5/1990 | Inacio et al. | 417/478 |

FOREIGN PATENT DOCUMENTS
34200861 4/1988 Fed. Rep. of Germany .
87/03492 6/1987 World Int. Prop. O. .

Primary Examiner—Richard A. Bertsch
Assistant Examiner—Peter Korytnyk
Attorney, Agent, or Firm—Fred Philpitt

[57] ABSTRACT

A fluid pump, particularly an extracorporeal blood pump, comprises a pump chamber (1) having an inlet opening (2) and an outlet opening (3), each connected to a respective non-return valve (4,5). The inlet (1) and the outlet (2) are movable in relation to each other and connected to a drive means (6) for periodic displacement of the inlet and the outlet alternately towards and away from each other, the interior volume of the pump chamber (1) being variable in correspondence with the relative distance between the inlet and the outlet. The pump chamber (1) is on its outside influenced by the surrounding pressure and has a wall of a flexible material constructed in such a manner that the pump chamber will collapse and reduce its volume, if the interior pressure in the pump falls below the surrounding pressure by an amount greater than the required opening pressure difference for the nomn-return valve connected to the inlet. The reduction of the interior volume of the pump chamber in the case of such collapsing will at least correspond to the maximum increase of the interior volume of the pump chamber when the inlet and outlet are moved away from each other.

14 Claims, 5 Drawing Sheets

FLUID PUMP WITH FLEXIBLE PUMP CHAMBER

BACKGROUND OF THE INVENTION

The present invention relates to an improved fluid pump, particularly for connection to the blood circulatory system of a living being.

The pump according to the invention has thus primarily been developed for use as an extracorporeal blood pump in conjunction, for instance, with surgical operations, dialysis, oxygenation of the blood in patients having an impaired lung function, for circulatory support after a cardiac insufficiency or for victims of accidents with heart or lung injuries, etc. It is also conceivable, however, for a pump according to the invention to be constructed in a manner which would enable it to be implanted in a patient as an artificial heart. It is also possible that a pump according to the invention could be advantageous to use also in other contexts, such as regional organ perfusion and/or organ perfusion in vitro.

Extracorporeal blood pumps used today for the above mentioned purposes are in the great majority of cases peristaltic so-called roller pumps, in which the blood is transported through a tube by rollers compressing the tube and simultaneously moving therealong. Recently a type of pulsatile pump has also begun to be used to a certain extent for the mentioned purposes, which pump basically consists of a pump bladder with flexible, resilient walls, which bladder has inlets and outlets provided with non-return valves and is enclosed in a surrounding rigid chamber, inside which a periodically varying pressure is generated for alternate compression and expansion of the pump bladder.

The peristaltic roller pumps have the serious drawback that it is very difficult to avoid considerable damages to the blood corpuscles in the pumped blood in consequence of the squeeze and shear forces that the blood corpuscles are subjected to in the pump.

The peristaltic roller pumps as well as the pulsatile pumps of the above mentioned type also have the common drawback that the operation of the pump will cause considerable subpressures at the inlet of the pump, and also in the pump bladder in the case of the pulsatile pump, if the inflow of blood to the pump inlet does not correspond to the nominal pumped flow of the pump but falls below it. Such a situation is liable to occur with relative ease, for example as a result of a blockage at the end of the catheter connecting the pump to a blood vessel, for instance by abutment of the catheter end with the wall of the blood vessel. The subpressure which in the hitherto used pumps in such cases is automatically generated on the inlet side of the pump and in the pump bladder may give rise to very troublesome problems. Thus, the subpressure may cause serious mechanical damages to the patient's blood vessels. Further, the subpressure may cause air to leak into the pump system through untight connections between various parts of the pump system, and if the subpressure is sufficient it may also result in gas being released from the pumped blood. In both cases serious gas emboli may occur. In the prior art blood pumps of the type discussed it is therefore necessary to monitor the pressure prevailing on the inlet side of the pump and in case of a subpressure intervene into the operation of the pump such that no serious situation may arise. Such a monitoring and control system will, of course, complicate and raise the price of the pump and will in itself constitute an additional source of possible malfunctions.

An attempt to avoid the above mentioned problems in roller and peristaltic pumps is disclosed in DE-C-3420861, describing a pump tubing made of a soft flexible material such that at a slight overpressure the tubing will take a form permitting throughflow of a fluid, and at a subpressure in relation to the ambient pressure the tubing will immediately collapse.

The basic construction and principle of a fluid pump of the type to which the present invention relates is described in WO 87/03492 (the disclosure of which is incorporated by reference herein).

SUMMARY AND OBJECTS OF THE INVENTION

The present invention thus relates to a fluid pump, particularly for connection to the blood circulatory system of a living being, of a type comprising a pump chamber having an inlet opening at one end and an outlet opening at the opposite end. A first non-return valve is connected to the inlet opening and permits a fluid flow only in the direction into the pump chamber through the inlet opening, and a second non-return valve is connected to the outlet opening and permits a fluid flow only in the direction out from the pump chamber through the outlet opening. The inlet and the outlet are movable in relation to each other in the direction of the pump chamber extension between the inlet and the outlet and are connected to controllable drive means for periodic displacement thereof alternately towards and away from each other in said direction of extension, the interior volume existing in the pump chamber between the inlet and outlet being variable in correspondence with the relative distance between them in said direction of extension.

In the case of a blood pump, such a pump may readily be constructed such that no mechanical damages will occur to the blood corpuscles in the pumped blood. The present invention is further based upon the discovery that in such a pump it is possible to automatically ensure, without any particular monitoring and control system, that no subpressure can be generated at the pump inlet or in the pump itself.

In accordance with the present invention this will be achieved by constructing a fluid pump of the above described type such that the pump chamber on the outside thereof is acted upon by the surrounding pressure (which e.g. may be the atmospheric pressure or the ambient pressure in a pressure chamber if the patient is subjected to such treatment), that it has a wall at least partially of a flexible material, and that it under the influence of a pressure difference, which is caused by the surrounding pressure exceeding the interior pressure of the pump chamber and which is greater than the required opening pressure difference for the first non-return valve connected to the inlet, is collapsible in a controlled manner by a volume at least corresponding to the maximum increase of said interior volume of the pump chamber when the inlet and the outlet are moved from each other.

BRIEF DESCRIPTION OF THE DRAWING

The invention will now be described in more detail with reference to the accompanying drawings which by way of example illustrate some preferred embodiments of a blood pump according to the invention, and wherein FIG. 1 schematically illustrates an axial section through one embodiment of the pump according to the invention at the end of a filling stroke for the pump chamber.

DESCRIPTION OF THE PREFERRED EMBODIMENTS

Figure 1:
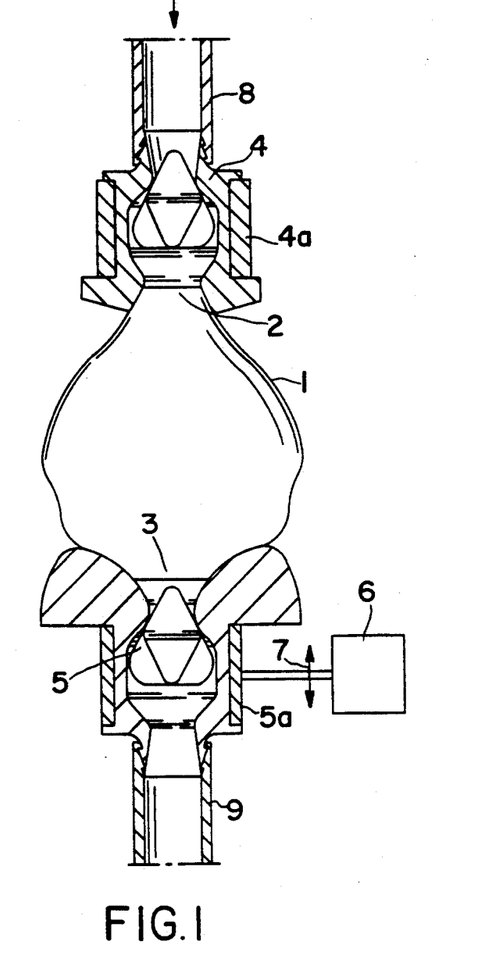
Figure 2:
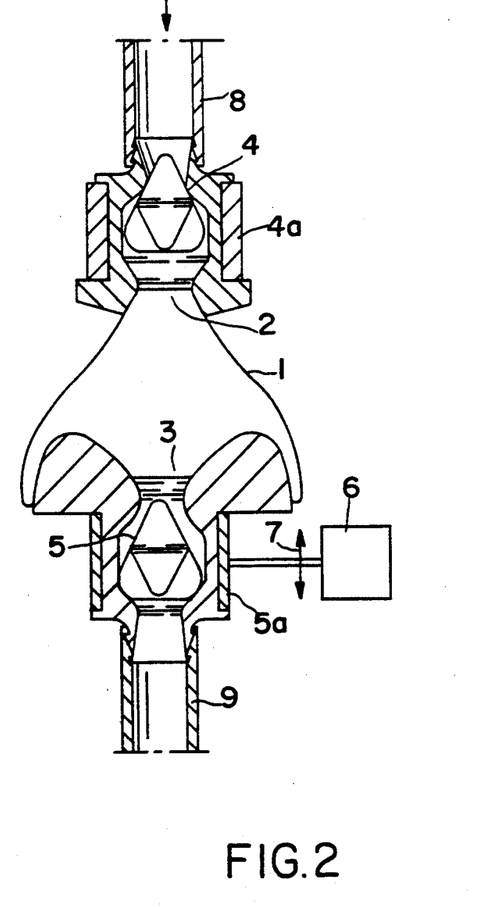
FIG. 2 schematically illustrates an axial section corresponding to that in FIG. 1 but at the end of a discharge stroke for the pump chamber.

The pump according to the invention illustrated schematically and by way of example in FIGS. 1 and 2 comprises a pump chamber 1 having an inlet 2 and an outlet 3 situated opposite to the inlet 2. Non-return valves 4 and 5 are connected to the inlet 2 and outlet 3, respectively, e.g. by gluing or ultrasonic welding, or by the valves being integral with the pump chamber. The valves 4 and 5 may, of course, be connected to the the respective inlet by any other suitable means, such as, for example, a mechanical compression type connection or the like. The two valves are arranged such that the inlet valve 4 only permits a flow into the pump chamber 1, while the outlet valve only permits a flow out from the pump chamber 1. In the illustrated embodiment the two non-return valves consist, as schematically shown, of movable valve bodies, which are acted upon by a closing force in a direction to sealing abutment against an associated valve seat, which closing force thus must be overcome for the valve to open. The closing force acting upon the valve body may, for example, consist of a spring force or of the weight of the valve body if the latter has a higher density than the pumped blood fluid, or as in the illustrated embodiment of the boyancy of the valve body in the pumped blood fluid as a result of the valve body having a lower density than the pumped blood fluid, or, finally, simply result from the blood pressure on the valves in the flow direction during the systolic (compression) and diastolic (relaxing) periods, respectively.

In the illustrated embodiment it is assumed that the inlet with the inlet valve 4 is stationarily arranged in an immobile holder 4a, while the outlet 3 with the outlet valve 5 is arranged in a holder 5a which is reciprocable in the longitudinal direction of the pump chamber 1, as is indicated by an arrow 7, when driven by a drive unit 6, constructed in a suitable manner, which is only indicated schematically and not shown in any detail. In the illustrated embodiment the pump chamber 1 is constructed as a substantially spherical bladder having flexible walls, which bladder, as will be described in more detail below, is constructed in such a manner as to enable part of its wall to be folded telescopically from the state shown in FIG. 1 to the state shown in FIG. 2, when the outlet 3 by means of the drive means 6 is moved between the greatest distance from the inlet 2, as shown in FIG. 1, and the smallest distance from the inlet 2, as shown in FIG. 2. The interior volume of the pump chamber or the pump bladder 1 thus varies in correspondence with the varying relative distance between the inlet 2 and the outlet 3.

Pumping takes place by the outlet 3 being periodically reciprocated in the direction of the arrow 7 by the drive means 6. During the filling stroke, i.e. when the outlet 3 is moved away from the inlet 2 to the position shown in FIG. 1, the volume of the pump chamber 1 is increased and blood flows into the pump chamber through the inlet valve 2 from the inlet tube 8 connected to the patient's blood circulatory system. It will be understood that the filling pressure for the pump chamber, which must be greater than the necessary opening pressure for the pump chamber, may be adjusted by varying the level of the pump chamber in relation to the patient. During the subsequent discharge stroke, i.e. when the outlet 3 is moved in the direction towards the inlet 2 to the position illustrated in FIG. 2, the volume of the pump chamber is reduced so that blood is pressed out through the outlet valve 5 to the outlet tube 9 connected to the patient's blood circulatory system. It will be understood that the blood volume pumped per unit of time may be determined and varied, respectively, by means of the frequency of the reciprocating movement of the outlet 3 and/or by the magnitude of the distance of movement of the outlet 3. It will also be appreciated that exactly the same function may be obtained by holding the outlet 3 stationary while periodically reciprocating the inlet 2 in the axial direction of the pump chamber 1. Alternatively, both the inlet 2 and the outlet 3 may also be periodically reciprocated in the axial direction of the pump chamber 1, enabling the blood volume pumped per unit of time to be varied by changing the relative phase position for these two periodical movements, maximum pumping being obtained when the two movements are in counter-phase, while no pumping at all is obtained when the two movements are in phase with each other.

From the above it will appear that if the blood supply through the inlet tube 8, when the pump is operated in the described manner, should cease or fall below the volume per unit of time that the pump strives to transport as a result of its operation; a gradually increasing subpressure will be generated in the inlet tube 8 and also in the pump chamber 1. As mentioned above such a subpressure may create very serious problems.

In the pump according to the invention the occurrence of such a subpressure is automatically avoided without it being necessary to influence the operation of the pump in any way. This is achieved by the pump chamber being constructed in such a manner that it will collapse, i.e. fall together reducing its interior volume, if the pressure prevailing in the pump chamber should fall below the ambient pressure acting upon the outside of the pump chamber with an amount exceeding the pressure difference between the inlet tube 8 and the interior of the pump chamber 1. The pump chamber 1 is in that respect constructed in such a way that its possible collapse and resulting volume reduction will be at least as great as the maximum volume increase during a filling stroke, i.e. during the movement of the outlet 3 from the position shown in FIG. 2 to the position shown in FIG. 1. It will be understood that as a result of this collapsibility of the pump chamber 1, the pressure within the pump chamber 1 and thereby the pressure in the inlet tube 8 will never fall below the surrounding (usually atmospheric) pressure by more than what corresponds to the necessary opening pressure for the inlet valve 4. Despite continued and unchanged operation of the pump, i.e. without any change of the periodic reciprocation of the outlet 3, the pump will not strive to pump a greater blood flow than that supplied through the inlet tube 8.

Figure 3:
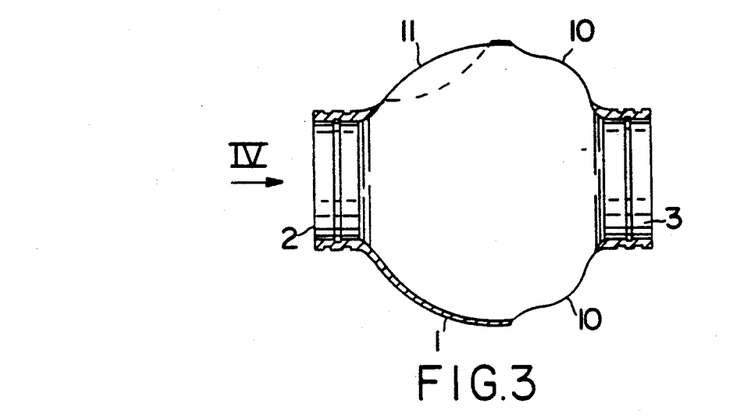
FIG. 3 illustrates a more detailed axial section through an advantageous embodiment of the pump chamber itself.
Figure 4:
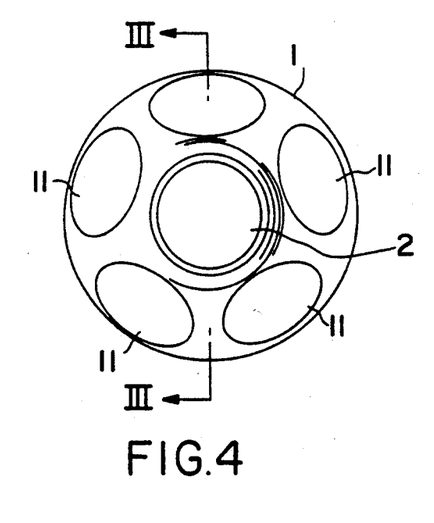
FIG. 4 illustrates an end view of the pump chamber according to FIG. 3 as seen in the direction indicated by an arrow IV in FIG. 3.

For the pump chamber 1 to be capable of varying its interior volume by telescopic folding in of its wall in the course of the periodic reciprocation of the outlet 3 and further be capable of collapsing to the necessary extent in the manner described above, without the pump chamber changing its configuration in such a way that it can not revert to its original configuration or continue to function in the manner intended, the pump chamber may advantageously be constructed in the way illustrated in FIGS. 3 and 4.

The advantageous embodiment of a pump chamber illustrated in FIGS. 3 and 4 is constructed as a generally spherical bladder having diametrically opposed inlet and outlet connection pieces 2 and 3, respectively, for mounting of the inlet and outlet valves not shown in FIGS. 3 and 4. The wall of the bladder 1 consists of a flexible but substantially non-stretchable material. On the side of the central diametrical plane between the inlet 2 and the outlet 3 which is situated closest to the outlet 3, the wall of the bladder 1 has an annular portion 10 which is concentric in relation to the centre axis of the bladder and has a substantially reduced wall thickness and a configuration slightly deviating from the spherical configuration in a double-wavy manner. Within this annular portion 10 the wall 1 of the bladder may be folded in telescopically in the manner shown in FIG. 2 in the course of the reciprocating movement of the outlet 3, without the configuration of the pump bladder being substantially changed in other respects. On the opposite side of said central diametrical plane, i.e. closest to the inlet 2, the wall of the bladder 1 is constructed with a number of generally circular portions 11, in the illustrated embodiment five such portions (FIG. 4), having a likewise substantially reduced wall thickness. Within these portions 11 the wall of the pump bladder may easily curve in, i.e. collapse, from the position indicated with a solid line to the position shown with a dashed line in FIG. 3, if the pressure within the pump bladder should fall below the surrounding atmospheric pressure with an amount greater than the necessary opening pressure for the inlet valve. In this case the wall portions 11 are adjusted in such a manner that the decrease of the interior volume of the pump bladder 1 caused by their collapse is at least as great as the maximum increase of the volume of the pump bladder when the outlet 3 moves from the position shown in FIG. 2 to the position shown in FIG. 1, i.e. during a filling stroke for the pump bladder. This collapse of the wall portions 11 of the pump bladder does not affect the configuration and function of the pump bladder in other respects.

It will, however, be understood from the aforegoing that also other constructions of the pump chamber are conceivable which permit the necessary collapsibility as well as the necessary variation of the interior volume of the pump chamber in dependence of the relative movement of the inlet and the outlet of the pump chamber. Thus, the collapsible wall portions may have other configurations and may also be located differently, e.g. in the opposite part of the pump bladder or be distributed over the whole or a major part of the pump bladder.

It will further be understood that the non-return valves do not necessarily have to be placed in immediate connection to the inlet and outlet, respectively, of the pump chamber, but could also be arranged at a distance from the pump chamber, for example in the inlet tube 8 and the outlet tube 9, respectively.

In a modified and advantageous embodiment of the blood pump the drive means is constructed so as to additionally ensure that no unpermissible overpressure can be generated at the pump outlet or in the pump itself. A drive means arrangement which prevents both unpermissible overpressures and unpermissible subpressures (by other means than a collapsible pump chamber) is described in our patent application Ser. No. 835,960 entitled "Blood pump with associated drive means" and filed simultaneously herewith (the disclosure of which is incorporated by reference herein). The combination thereof with the present invention, primarily relating to the collapsibility of the pump chamber in a pump of the type in question, is illustrated in FIGS. 5 and 6 wherein corresponding parts to those in FIGS. 1 to 4 are provided with the same reference numerals.

Figure 5:
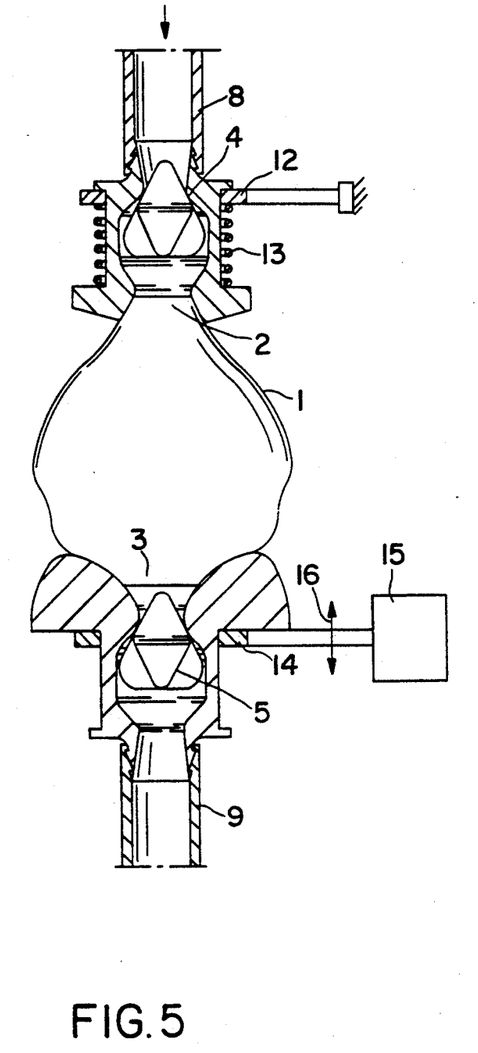
FIG. 5 schematically illustrates an axial section through a modified embodiment of the blood pump at the end of a filling stroke for the pump chamber.
Figure 6:
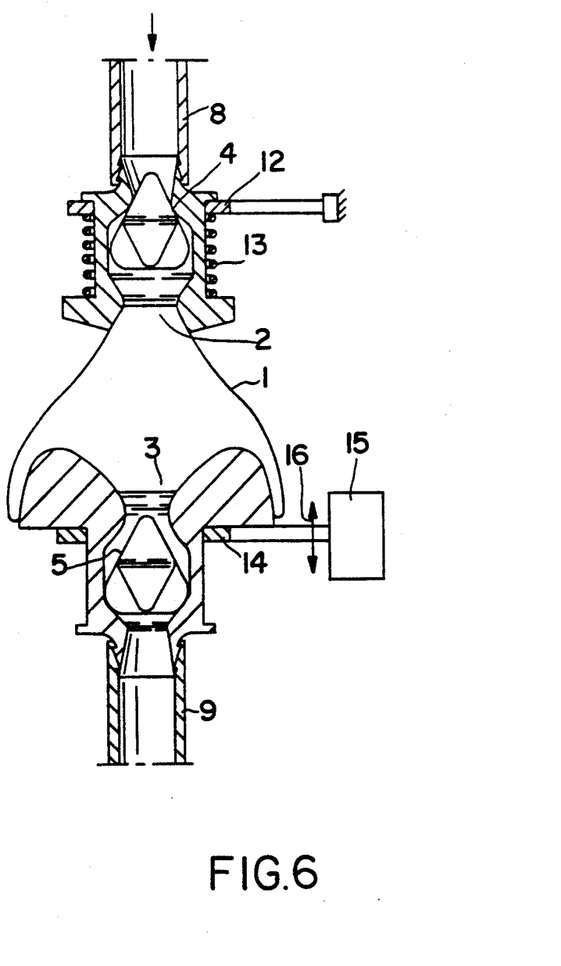
FIG. 6 schematically illustrates an axial section corresponding to that in FIG. 5 but at the end of a discharge stroke for the pump chamber.

As in the embodiment illustrated in FIGS. 1 and 2, the inlet 2 with the inlet valve 4 and the outlet 3 with the outlet valve 5 are reciprocatingly displaceable in relation to each other by a drive means between the most brought apart position illustrated in FIG. 5 and the most brought together position illustrated in FIG. 6. In the case of the embodiment illustrated in FIGS. 5 and 6 of the drive means for the pump, the inlet 2 with the inlet valve 4 is arranged in an annular holder 12 which is stationarily mounted in a suitable manner not shown in any detail. The inlet 2 with the inlet valve 4 is axially movable in relation to the holder 12 through a limited distance corresponding to the length of the maximum desired relative movement between the inlet 2 and the outlet 3. Further, a spring means 13, only illustrated schematically and the spring force of which preferably is adjustable, is arranged between the holder 12 and the inlet 2 with the inlet valve 4. The outlet 3 with the outlet valve 5 is similarly arranged in an annular holder 14 and is axially movable in relation to this holder 14 through a distance corresponding to the length of the maximum desired relative movement between the inlet 2 and the outlet 3. The holder 14 is movable in the axial direction of the pump chamber 1 and connected to a suitable drive mechanism 15, only illustrated schematically and not in any detail, by which drive mechanism the holder 14 may be forcibly driven reciprocatingly by a suitable drive motor as is indicated by an arrow 16 with a desired frequency and with a distance of movement corresponding to the maximum desired relative displacement between the inlet 2 and the outlet 3.

The described drive means for the pump operates in the following way. When the holder 14 during a filling stroke for the pump chamber 1 is forcibly moved by the drive mechanism 15 in the direction downwards from the position shown in FIG. 6 to the position shown in FIG. 5, the outlet 3 with the outlet valve 5 will normally accompany the downward movement of the holder 14 under the influence of its own weight and the weight of the blood present in the pump chamber 1. This total weight, which optionally may be assisted by an additional and predetermined spring force as will be described in more detail below, is adapted not to substantially exceed the necessary opening pressure for the inlet valve 4. The latter is accordingly opened and blood flows into the pump chamber 1 from the inlet tube 8 so that the volume of the pump chamber 1 is increased and the outlet 3 with the outlet valve 5 can accompany the holder 14 in the downward movement thereof. It will, however, be appreciated that blood may flow into and fill the pump chamber 1 in this manner only to the extent as blood is supplied through the inlet tube 8. If the blood supply through the inlet tube is too small, the outlet 3 with the outlet valve 5 will not be able to accompany the downward movement of the holder 14 to the full extent. If the blood supply through the inlet tube 8 is completely stopped, the outlet 3 with the outlet valve 5 will remain in the position illustrated in FIG. 6, while the holder 14 is moved downwards by the drive mechanism 15. It will be appreciated that the subpressure that may arise in the inlet tube 8 in relation to the ambient (usually atmospheric) pressure can never exceed a value corresponding to the weight of the outlet 3 with the outlet valve 5 and of the blood quantity that is present in the pump chamber 1 in the position illustrated in FIG. 6. The pump will consequently never strive to pump a larger quantity of blood than is supplied through the inlet tube 8, and if this blood supply is interrupted completely, the effective pumping also stops automatically without the necessity of influencing the driving of the holder 14 by means of the drive mechanism 15 in any way and without permitting any uncontrolled substantial subpressure to be generated in the inlet tube 8 or in the pump chamber 1. If the blood supply through the inlet tube 8 is interrupted completely, the outlet 3 with the outlet valve 5 and the pump chamber 1 will remain in the state illustrated in FIG. 6, while the holder 14 may be reciprocated by means of the drive mechanism 15. Further safety against subpressures will, of course, be ensured by the collapsability of the pump chamber 1 as described above with reference to FIGS. 1 to 4.

The relative separating force between the inlet 2 and the outlet 3, which in the illustrated embodiment is generated by the weight of the outlet 3 with the outlet valve 5 and the blood in the pump chamber 1, may naturally also and equally well be generated by means of a spring member acting between the inlet 2 and the outlet 3. This may in particular be suitable if the pump is oriented in another way than in the embodiment illustrated, such as horizontally. It is, of course, also possible to balance the aforesaid gravity completely or partially with an opposing spring force, if suitable. Examples of such embodiments of the pump are illustrated in FIGS. 7 to 10 and will be described further on.

When during a discharge stroke for the pump chamber 1 the holder 14 is driven upwards by the drive mechanism 15 from the position illustrated in FIG. 5 to the position illustrated in FIG. 6, the inlet 2 with the inlet valve 4 is normally stationary due to a suitably adjusted bias of the spring 13, and the volume of the pump chamber 1 is therefore reduced from that shown in FIG. 5 to that shown in FIG. 6 and blood is pressed out from the pump chamber 1 through the outlet valve 5 to the outlet tube 9. Should the resistance to the blood flow through the outlet tube 9 then be so great that the pressure in the pump chamber 1 will tend to exceed the biasing force of the spring means 13, this spring means will begin being compressed and the inlet 2 with the inlet valve 4 will therefore begin to move upwards relative to the stationary holder 12. The pressure in the pump chamber 1, and thereby in the outlet tube 9 in the course of the discharge stroke for the pump chamber, may thus never exceed a value corresponding to the spring force of the spring means 13. If there is a complete blockage of the blood flow in the outlet tube 9, the inlet 2 with the inlet valve 4 will completely accompany the movement of the outlet 3 with the outlet valve 5 while being driven by the drive mechanism 15, whereby the effective pumping ceases completely without the necessity of influencing the driving of the holder 14 by means of the drive mechanism 15 and without the overpressure in the pump chamber 1 and thereby the outlet tube 9 exceeding a value corresponding to the spring force of the spring means 13 in the most compressed state thereof. The spring means 13 is thus suitably constructed in such a manner that its bias in the non-compressed state corresponds to the highest pressure that should normally exist in the outlet tube 9 and that its maximum spring force in the maximally compressed state corresponds to the highest overpressure in the outlet tube 9 that can be permitted. It will be understood that the spring means 13 may be constructed in such a manner as to enable both its biasing force and its maximum spring force as well as its characteristic between these two values to be varied or set depending on the use in question of the pump, for example depending on which circulatory system of a patient that the pump is to be connected to. It is to be noted that the illustrated location of the spring means 13 is only exemplary and for ease of illustration and that the same function may be obtained if the spring means are arranged otherwise, e.g. in the actual drive mechanism.

Figure 7:
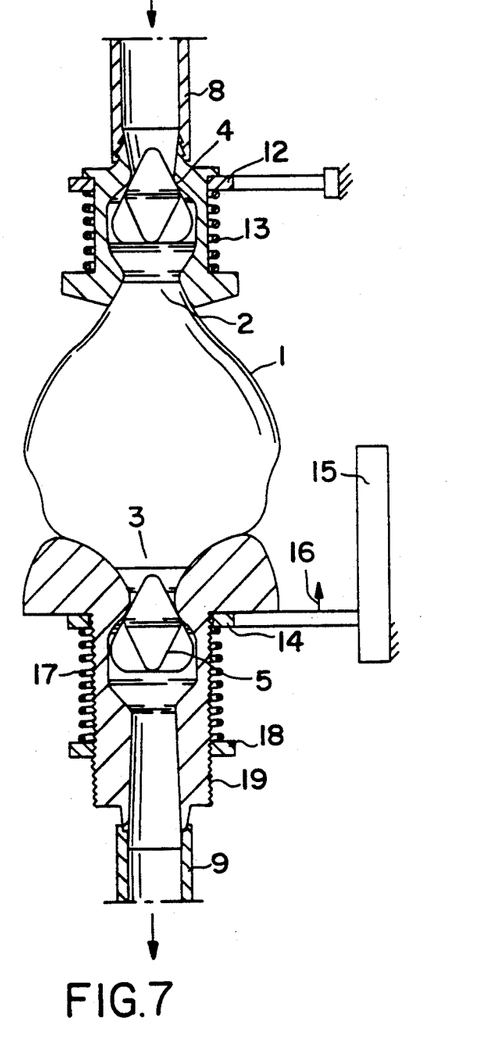
FIG. 7 illustrates an axial section through another embodiment of a blood pump according to the invention at the end of a filling stroke for the pump chamber.
Figure 8:
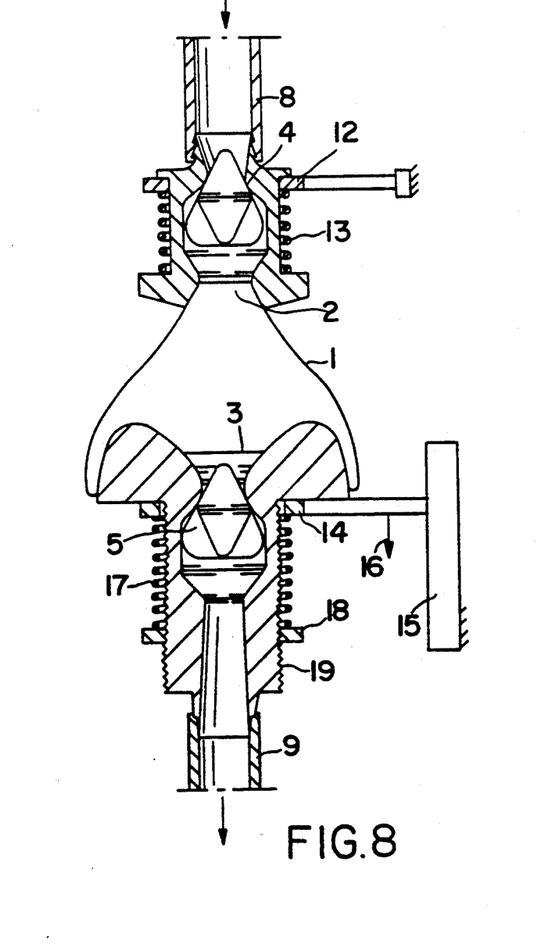
FIG. 8 illustrates an axial section corresponding to that in FIG. 7 but at the end of a discharge stroke for the pump chamber.

Reference is now made to FIGS. 7 to 10 wherein corresponding parts are provided with the same reference designations as before. FIGS. 7 and 8 illustrate the pump according to FIGS. 5 and 6 modified by the addition of a spring means 17 acting between the holder 14 and a support 18 attached to an extended outlet portion 19 of the pump chamber. The support 18 is preferably a nut member threadedly engaged with the outlet portion 19 to permit the spring means to be suitably biased. When the holder 14 is moved downwards from the position illustrated in FIG. 8 to the position illustrated in FIG. 7, the outlet 3 with the outlet valve 5 will normally accompany the downward movement of the holder 14. Should, however, e.g. due to a decrease or blockage of the inflow of blood to the inlet 2, a subpressure tend to be created in the pump chamber 1, the spring means 17 will be compressed and the outlet 3 remain stationary. The maximum subpressure that may be created in the pump chamber is thus determined by the spring force of the spring means 17 when the latter is in its most compressed state, i.e. when the holder 14 is in its lowest position. This spring force may be suitably set by adjusting the vertical position of the nut member 18.

Figure 9:
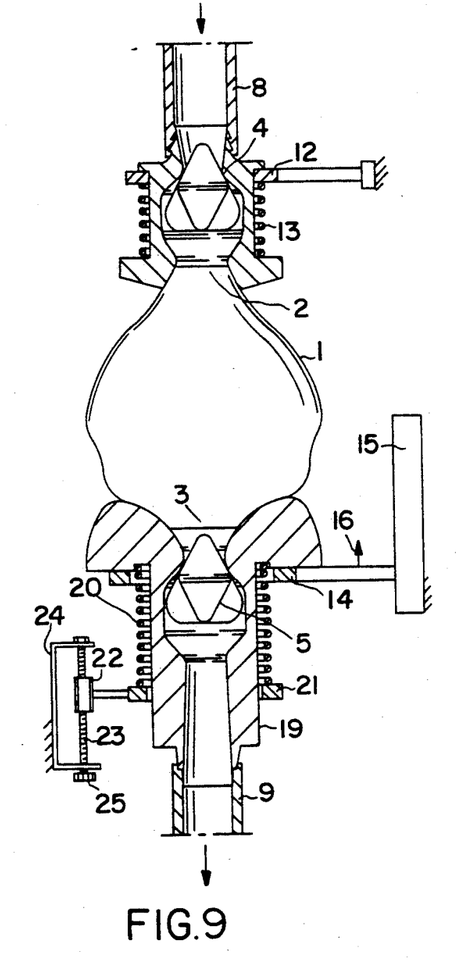
FIG. 9 illustrates an axial section through still another embodiment of a blood pump according to the invention at the end of a filling stroke for the pump chamber.
Figure 10:
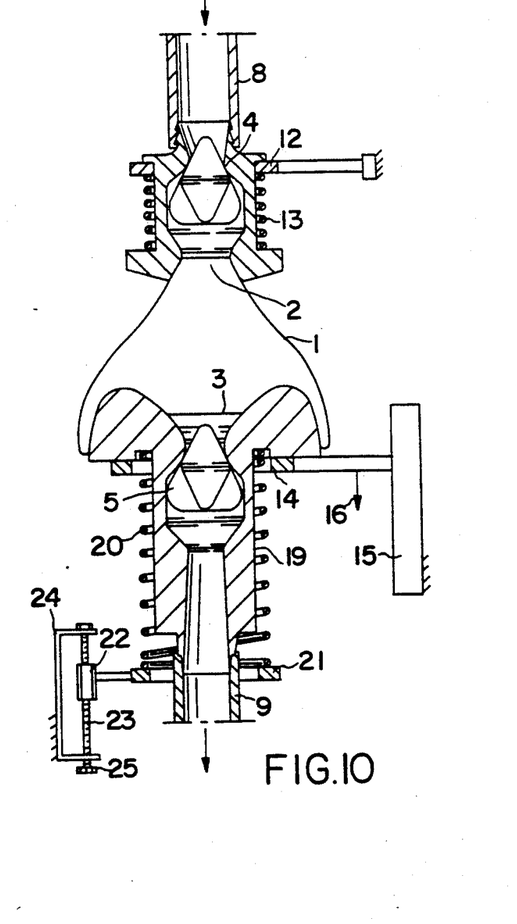
FIG. 10 illustrates an axial section corresponding to that in FIG. 9 but at the end of a discharge stroke for the pump chamber.

FIGS. 9 and 10 illustrate a variation of the embodiment in FIGS. 7 and 8 wherein the separating force acting upon the outlet portion of the pump chamber is totally independent of the movement of the holder 14. In this embodiment a spring means 20 is attached at its upper end to the outlet part 3 of the pump chamber 1 and at its lower end to an annular support 21 surrounding the extended outlet portion and freely movable in relation thereto. The support 21 is in turn fixed to a nut member 22 threadedly engaged with a screw 23 rotatably mounted in a stationary bracket 24. Through vertical adjustment of the nut member 22 by rotation of the screw head 25 of the screw 23, the spring means 20 may be biased as desired. When the holder 14 is moved downwards from the position shown in FIG. 10 to the position shown in FIG. 9, the spring means 20, as adjusted in the figures, will successively contract exerting a defined separating force between the inlet 2 and the outlet 3. The maximum subpressure created thereby in the pump chamber will correspond to the maximum spring force, and a desired maximum subpressure level in the pump chamber may thus be set by adjustment of the vertical position of the support 21. It will be understood that the spring means 20 may also, if desired, be adjusted to partially or completely balance the gravitational force of the outlet 3 with the outlet valve 5 and the blood quantity present in the pump chamber 1.

With reference to all the embodiments described above and presented in the drawings it will be understood that the described function of the pump will also be obtained if the holder 14 for the outlet 3 with the outlet valve 5 is stationary, while the holder 12 for the inlet 2 with the inlet valve 4 is instead forcibly reciprocated by means of the drive mechanism 15. The same functional mode will also be obtained if the two holders 12 and 14 are movable and reciprocated by means of a common drive mechanism or individual drive mechanisms, the sum of the distances of movement of the two holders corresponding to the maximally desired relative displacement between the inlet 2 and the outlet 3 of the pump chamber 1. The movement distance of each holder may, for example, correspond to half the maximally desired displacement between the inlet and the outlet. In the case of such a construction of the drive means the magnitude of the pumped flow may be varied, not only by varying the frequency and stroke length of the driving, but also by changing the relative phase position of the drivings of the two holders 12, 14, a maximum pumped flow being obtained when the holders 12, 14 move in counter-phase, while the effective pumping will be zero if the holders 12 and 14 are driven in phase with each other.

It will be understood from the foregoing that if the effective pumping substantially ceases in the manner described above due to the blood supply through the inlet tube 8 being choked or the blood flow out through the outlet tube 9 being choked, the blood present in the pump chamber 1 and the non-return valves will in spite thereof be maintained in a certain movement as a result of the continued operation of the pump by means of the drive mechanism 15. This is of essential importance to prevent coagulation of the blood. It will also be appreciated that the pump according to the invention also involves the very important advantage that when the pump is in use, for example in conjunction with a surgical procedure, the effective pumping can be stopped at any time by closing either the inlet tube 8 or the outlet tube 9 with a forceps, and then starting the pumping again by removing the forceps, without the operation of the pump by means of its drive means having to be influenced in any way and without any risk that neither unpermissible subpressures nor unpermissible overpressures may be created.

The invention is, of course, not restricted to the embodiments specifically described above and illustrated in the drawings, and several changes and modifications may be made within the scope of the present inventive concept as defined in the following claims.

We claim:

1. A fluid pump, particularly for connection to the blood circulatory system of a living being, comprising a pump chamber (1) having an inlet opening (2) at one end thereof and an outlet opening (3) at the opposite end thereof, a first non-return valve (4) connected to the inlet opening and permitting a fluid flow only in the direction into the pump chamber (1) through the inlet opening, and a second non-return valve (5) connected to the outlet opening and permitting a fluid flow only in the direction out from the pump chamber (1) through the outlet opening, the inlet and the outlet (2, 3) being movable in relation to each other in the direction of the extension of the pump chamber (1) between the inlet and the outlet (2, 3) and being connected to controllable drive means (6; 12, 13, 14, 15) for periodic movement thereof alternately towards and away from each other in said direction of extension, the interior volume existing in the pump chamber (1) between the inlet (2) and outlet (3) being variable in correspondence with the relative distance between them in said direction of extension, characterized in that the pump chamber (1) on the outside thereof is acted upon by the surrounding pressure, that it has a wall at least partially of a flexible material, and that it under the influence of a pressure difference, which is caused by the surrounding pressure exceeding the interior pressure of the pump chamber (1) and which is greater than the required opening pressure difference for the first non-return valve (4) connected to the inlet (2), is collapsible by a volume at least corresponding to the maximum increase of said interior volume of the pump chamber when the inlet (2) and the outlet (3) are moved away from each other, said collapsibility being provided by one or more defined wall portions (11) having a reduced wall thickness.

2. A fluid pump, particularly for connection to the blood circulatory system of a living being, comprising a pump chamber (1) having an inlet opening (2) at one end thereof and an outlet opening (3) at the opposite end thereof, a first non-return valve (4) connected to the inlet opening and permitting a fluid flow only in the direction into the pump chamber (1) through the inlet opening, and a second non-return valve (5) connected to the outlet opening and permitting a fluid flow only in the direction out from the pump chamber (1) through the outlet opening, the inlet and the outlet (2, 3) being movable in relation to each other in the direction of the extension of the pump chamber (1) between the inlet and the outlet (2, 3) and being connected to controllable drive means (6; 12, 13, 14, 15) for periodic movement thereof alternatively towards and away from each other in said direction of extension, the interior volume existing in the pump chamber (1) between the inlet (2) and outlet (3) being variable in correspondence with the relative distance between them in said direction of extension, characterized in that the pump chamber (1) on the outside thereof is acted upon by the surrounding pressure, that it has a wall at least partially of a flexible material, and that it under the influence of a pressure difference, which is caused by the surrounding pressure exceeding the interior pressure of the pump chamber (1) and which is greater than the required opening pressure difference for the first non-return valve (4) connected to the inlet (2), is collapsible by a volume at least corresponding to the maximum increase of said interior volume of the pump chamber when the inlet (2) and the outlet (3) are moved away from each other, said collapsibility being provided by one nor more defined wall portions (11) having a reduced wall thickness.

3. A pump according to claim 1, characterized in that the wall of the pump chamber (1) is substantially non-stretchable.

4. A pump according to claim 1, characterized in that said collapsible wall potions (11) are substantially evenly distributed over at least part of the pump chamber (1).

5. A pump according to claim 1, characterized in that the pump chamber (1) has a substantially spherical configuration with diametrically opposed inlet and outlet openings (2, 3) the flexible wall of the pump chamber (1) on one side of the diametrical plane located substantially right between the inlet and outlet openings being constructed with an annular portion extending substantially in parallel with said diametrical plane (1) and having a wall thickness so as to enable the wall within this portion to fold telescopically when the inlet and outlet openings are moved in the direction towards each other, and the flexible wall on the other side of said diametrical plane being constructed with a number of, preferably substantially circular, additional portions (11) with a reduced wall thickness, which are substantially evenly distributed around the pump chamber, which wall portions are capable of easily being curved in under the influence of a small overpressure on the outside of the wall relative to the pressure on the inside thereof and thereby provide the pump chamber (1) with the necessary collapsibility.

6. A pump according to claim 1 characterized in that said drive means arrangement (12, 13, 14, 15) has such a mechanical construction that the contracting force exerted between the inlet (2) and the outlet (3) of the pump chamber (1), when the outlet (3) and the inlet (2) are moved in the direction towards each other during the discharge stroke of the pump chamber (1) cannot exceed a predetermined maximum value corresponding to a predetermined maximum permissible pressure on the outlet side of the pump chamber (1).

7. A pump according to claim 1, characterized in that said drive means arrangement (12, 13, 14, 15) has such a mechanical construction that the separating force exerted between the outlet (3) and the inlet (2) of the pump chamber (1), when the outlet (3) and the inlet (2) are moved in the direction away from each other during the filling stroke of the pump chamber (1), cannot exceed an amount corresponding to a predetermined maximum permissible pressure difference between the surrounding pressure and the interior pressure of the pump chamber (1), thereby preventing the generation of any excessive uncontrolled negative pressure within the pump chamber.

8. A pump according to claim 7, characterized in that the inlet (2) and the outlet (3) of the pump chamber are acted upon by a relative separating force independent of the relative movement and operation of the drive means (12, 13, 14, 15).

9. A pump according to claim 7, characterized in that said separating force is a gravitational force.

10. A pump according to claim 7, characterized in that said separating force is or includes a spring force.

11. A pump according to claim 7, characterized in that the separating force exerted between the inlet (2) and the outlet (3) of the pump chamber (1) during the filling stroke of the pump chamber is provided by said drive means (14) acting upon the outlet part (3, 18, 19) of the pump chamber via an intermediate compression spring means (17) such that the maximum separating force that may be exerted is restricted to the spring force of said spring means.

12. A pump according to claim 1, characterized in that said drive means comprises two drive elements (12, 14) forcibly reciprocatable in relation to each other in said direction of extension of the pump chamber (1), the relative distance of displacement of said drive elements corresponding to the maximum desired relative displacement between the inlet (2) and outlet (3) of the pump chamber, and said two drive elements (12, 14) being connected to the inlet (2) and outlet (3), respectively, of the pump chamber in such a way that the inlet and the outlet, respectively, are restrictedly movable in relation to the respective drive element through a distance having a length corresponding to the maximum desired relative displacement between the inlet and outlet; and that spring means (13) are arranged, preferably coupled into the force transmitting path between one of said drive elements (12) and the part (2) of the pump chamber (1) which is connected thereto, in such manner that the spring means is compressed if the contracting force exerted between the inlet (2) and the outlet (3) of the pump chamber during a discharge stroke of the pump chamber tends to exceed a predetermined value and thereby restricts said force to correspond to the spring force of the spring means (13).

13. A pump according to claim 12, characterized in that one drive element (12) is stationary while the other drive element (14) is forcibly reciprocatable through a distance corresponding to the maximum desired relative displacement between the inlet (2) and outlet (3) of the pump chamber.

14. A pump according to claim 12, characterized in that both the drive elements (12, 14) are movable and forcibly reciprocatable, the sum of the movement distances of the two drive elements corresponding to the maximum desired relative displacement between the inlet (2) and outlet (3) of the pump chamber.

* * * * *